United States Patent [19]

Fruehwirth

[11] Patent Number: Plant 7,275

[45] Date of Patent: Jul. 17, 1990

[54] POINSETTIA PLANT '268'

[75] Inventor: Franz Fruehwirth, Encinitas, Calif.

[73] Assignee: Paul Ecke Ranch, Inc., Encinitas, Calif.

[21] Appl. No.: 263,155

[22] Filed: Oct. 27, 1988

[51] Int. Cl.[5] ..... A01H 5/00
[52] U.S. Cl. ..... Plt./86
[58] Field of Search ..... Plt./86

[56] References Cited

U.S. PATENT DOCUMENTS 4,724,276 2/1988 Ecke, Jr. ..... 800/1

*Primary Examiner*—James R. Feyrer
*Attorney, Agent, or Firm*—Arnold, White & Durkee

[57] ABSTRACT

The Poinsettia cultivar of the present invention, '268', is distinguished by its large, bright red bracts which tend to remain erect, even upon commercial shipping. '268' originated as a sport of the seedling 'C-27', which can be grown in a relatively cool greenhouse, making it more economical to grow commercially. '268' displays self-branching traits not present in 'C-27'.

1 Drawing Sheet

BACKGROUND OF THE INVENTION

Poinsettia, cultivar '268', is a sport of cultivar 'C-27' with large, bright red erect flower bracts. It branches more freely than 'C-27' but retains its desirable flower characteristics. '268' is unique because the flower bracts remain erect and do not droop even after commercial shipping and handling or as the flowers mature. It always looks "fresh" which adds to its beauty and increases its value as a consumer product. Poinsettia '268' can be grown in a relatively cool greenhouse, making it more economical to grow commercially.

This new poinsettia cultivar originated as a sport of the seedling 'C-27' in a greenhouse in Encinitas, Calif. It was selected from many plants because of its large erect flower bracts and self-branching traits which distinguish it from other poinsettia cultivars, and seem to make it a desirable plant for commercial greenhouse production. After selection, vegetatively reproduction of this plant by stem cuttings for test purposes in Encinitas, Calif., and clones of the plant were subjected to successive generations of vegetative propagation which demonstrated that its distinct characteristics hold true from generation to generation. The plant height of '268' is somewhat shorter than that of 'C-27'. Under the same cultural and environmental conditions, the relative shortness of '268' offers certain economic advantages over 'C-27', in that, less growth retarding chemicals need to be applied to control undesirable plant height.

DESCRIPTION OF THE PHOTOGRAPHS

Poinsettia '268' is illustrated in the accompanying color photographs. The lower photo is a side view of '268' plants, left, with its several flowering side branches and 'C-27', right, in full flower. The upper photo is a top view of the '268' plants showing flower and bract formation.

DESCRIPTION OF THE PLANT

The following is a detailed description of this new poinsettia as observed in a greenhouse in Encinitas, Calif., during December, 1987. Recorded observations from flowering plants, grown as 3 unpinched plants per pot were observed. The pot was 14 cm. in diameter and 11 cm. in height. Color designations were compared to the 1986 edition of R.H.S. Colour Chart, first published in 1966 by The Royal Horticultural Society, London, England.

THE PLANT

Origin: Sport of 'C-27', the sport was induced by application of the procedures set forth in U.S. Pat. No. 4,724,276 to the parent plant 'C-27'.

Classification:

*Botanic.*—*Euphorbia pulcherrima* Willd.
*Common name.*—Poinsettia.
*Cultivar name.*—'268'.

Form: Shrub.

Height: Short to medium somewhat shorter than 'C-27'.

Growth habit: As a single stemmed plant, upright and vigorous with several self-branching axillary stems. The application of a chemical growth retardant may not be needed to restrict height for commercial pot plant production. Observation of 3 plants in a pot with an overall height of 35 cm. and an overall width of 48 cm. were made. The bract diameter of individual flowers was 32 cm.

Branching: Branching can be enhanced by removal of the stem tip. Then, several flowering branches with equal vigor will develop on a single plant. Poinsettia '268', unlike its parent plant 'C-27', has self-branching traits. Axillary branches will develop and terminate in a flower without pinching. In contrast, axillary branches develop on the parent plant 'C-27', only where terminal dominance is removed by pinching. It may be desirable to pinch '268' and remove all terminal dominance. Then, all axillary branches will develop uniformly and at a faster rate. Also, after pinching, '268' may develop 6 to 8 or more axillary shoots, whereas on the parent plant 'C-27', only 3 to 5 axillary branches will typically develop after pinching.

Growth rate: Very fast. Rooting of stem cuttings occurs in 12–18 days under intermittent mist. The plant will flower in about nine weeks under continuous long night conditions and night temperatures of about 16–18 degrees C.

Foliage: The foliage is clean and uniformly green from bottom to top of the plant. The leaves are of medium size, leaf blades typically being about 11–12 cm. long and about 9–10 cm. wide with leaf petioles about 5–6 cm. long.

Leaf shape: Typical leaves are ovate with obtuse bases and acuminate tips. Leaf margins are mostly lobed with 2 indentations on each side of the leaf blade. The leaf shape of '268' is less serrated or lobed than the leaves of 'C-27'. Furthermore, the leaves of '268' are wider in proportion to the length than those of 'C-27'.

Color:

*Upper side.*—Green, near R.H.S. 147A.

*Under side.*—Between R.H.S. 138A and R.H.S. 138B.

Retention: The foliage lasts fairly well even under low tight intensities in the consumer's home.

Bracts: Generally there are 18–24 uniformly colored bracts of various sizes subtending the cyathia. The primary bracts have blades typically 15–17 cm. long and 10–11 cm. wide with petioles about 3 cm. long. Bract attitude is similar for both '268' and its parent 'C-27'. Most cultural requirements are the same, such as temperature, light intensity and nutrition. However, commercially, '268' would be more acceptable as a pinched plant, whereas its parent 'C-27', will be more suitable for a non-pinched plant.

Shape: Bracts are mostly ovate with acute bases and acuminate tips. Primary bracts are lobed with two indentations on either side of the bract. Secondary bracts have entire margins. The bract shape of '268' is less serrated or lobed than the bracts of 'C-27'. Furthermore, the bracts of '268' are wider in proportion to length than those of 'C-27', and usually slightly less lobed.

Color:

*Upper side.*—Bright red, darker than R.H.S. 46B or R.H.S. 45A.

*Under side.*—Red, near R.H.S. 47A and R.H.S. 53C.

The color intensity of the red bracts of '268' is not quite as bright as that of the 'C-27' parent.

Flowers: Generally, 12–15 cyathia (flowers) are present when the plant is in "full bloom". Each cyathium is about 8 mm long and about 5 mm wide, light green in color, and fringed with red at the distal end. Usually one bright yellow nector cup protrudes from the side of each cyathium. The flower pedicel is also light green and about 5–6 mm in length. The anther protruding from the cyathia are red. The flowers of '268' appear to be the same in every respect to those of the parent plant 'C-27', except that the flower response time is slightly shorter for '268'. '268' may come to "full bloom" 3–5 days before 'C-27'.

What is claimed:

1. A new and distinct Poinsettia cultivar, substantially as herein shown and described, distinguished by its large, bright red, flower bracts which tend to remain erect, and its self-branching traits.

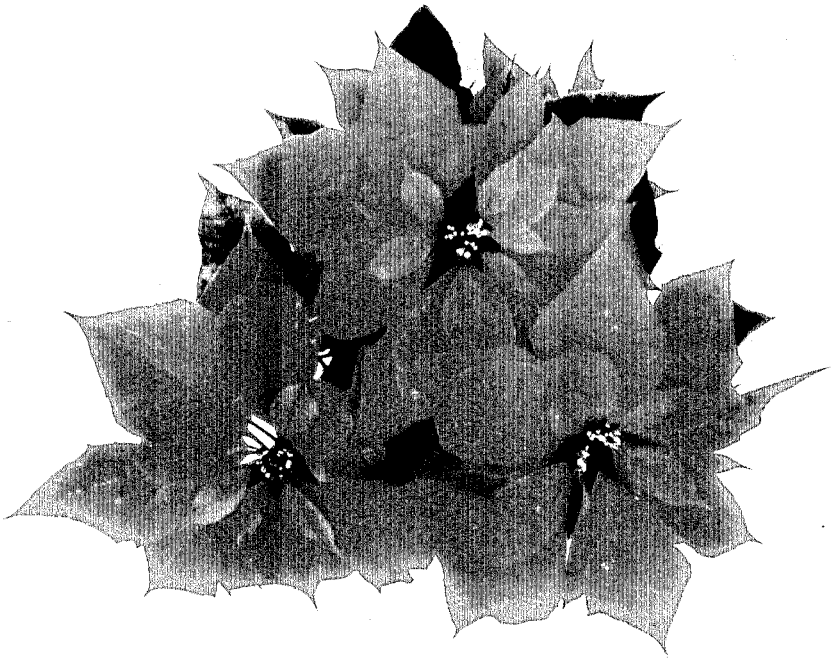
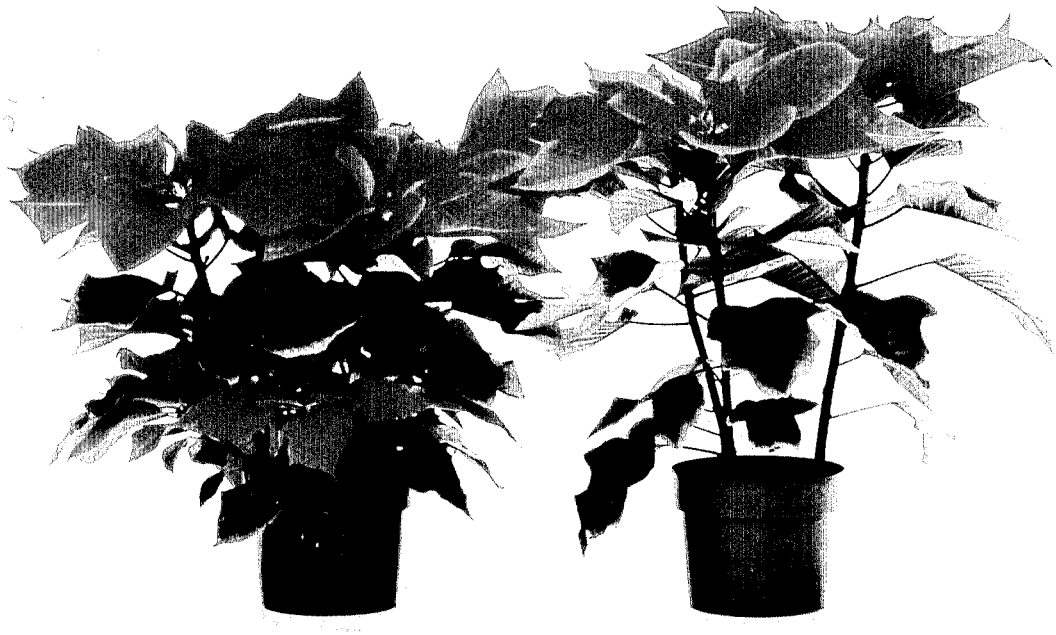

* * * * *